United States Patent [19]

Nishimura et al.

[11] Patent Number: 4,842,863

[45] Date of Patent: Jun. 27, 1989

[54] GRANULAR AGENT FOR RUMINANT AND PRODUCTION METHOD THEREOF

[75] Inventors: Kunio Nishimura; Hitoshi Iijima, both of Kawasaki, Japan

[73] Assignee: Showa Denko Kabushiki Kaisha, Tokyo, Japan

[21] Appl. No.: 148,524

[22] Filed: Jan. 26, 1988

[30] Foreign Application Priority Data

Jan. 26, 1987 [JP] Japan .................................. 62-13999

[51] Int. Cl.⁴ .............................................. A23K 2/00
[52] U.S. Cl. .................................... 424/438; 424/498; 424/502
[58] Field of Search ......................................... 424/438

[56] References Cited

U.S. PATENT DOCUMENTS 4,687,676 8/1987 Wu et al. .............................. 424/438
4,713,245 12/1987 Ando et al. .......................... 424/438

Primary Examiner—Thurman K. Page
Assistant Examiner—Leon R. Horne
Attorney, Agent, or Firm—Sughrue, Mion, Zinn, Macpeak, and Seas

[57] ABSTRACT

A granular agent for a ruminant comprising a solid substance containing at least one physiologically active substance coated with a thin film of a waxy substance having a melting point of 40° C. to 120° C., the thin film having a thickness of 0.2 to 20 μm and containing therein fine solid particles having a melting point of 120° C. or more and an average particle size of 10 μm or less and the fine solid particles being substantially slightly soluble in water and insoluble in the waxy substance under a neutral condition.

5 Claims, 1 Drawing Sheet

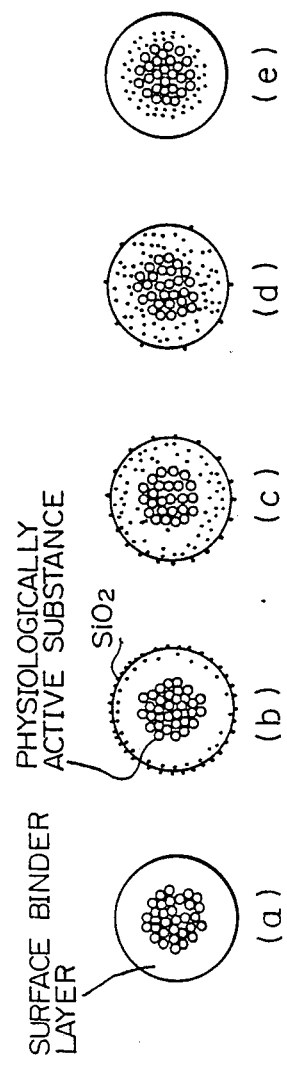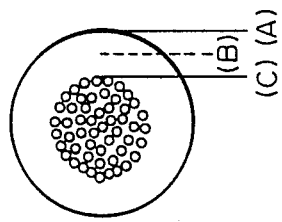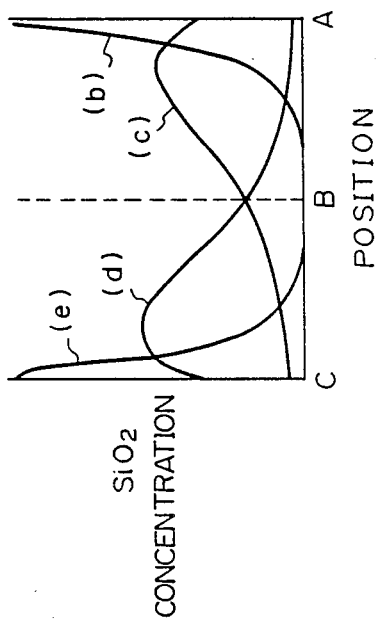

GRANULAR AGENT FOR RUMINANT AND PRODUCTION METHOD THEREOF

BACKGROUND OF THE INVENTION

1. Field of the Invention

The present invention relates to a granular agent for a ruminant and containing a physiologically active substance, and a production method thereof. More specifically, it relates to a granular agent for a ruminant in which a physiologically active substance usually fed with, for example, an animal feed, is protected from the action of microorganisms present in a rumen of a ruminant and is digested and absorbed in an abomasum and downstream thereof, and a production method thereof.

2. Description of the Related Art

For example, in ruminants such as cattles and sheep, a vriety of microorganisms are present in a rumen and, therefore, cellulose and other components, which cannot be inherently digested in the higher animals, are utilized with the assistance of the action of the microorganisms. However, when physiologically active substances such as amino acids and proteins are orally fed, most of those substances are decomposed by the organism in a rumen to lose their physiological activities and, therefore, these physiologically active substances cannot be effectively utilized.

Thus, a so-called rumen-by-pass granular agent, i.e., an agent which is not solubilized in a rumen and is dissolved and absorbed in an abomasum and downstream thereof, is important to effectively utilize physiologically active substances in ruminants. Various such granular agents have been developed and utilized in the fields of, for example, animal feed, nutrients, and drugs.

The conventional rumen-by-pass agents for ruminants are generally produced by coating physiologically active substances with protective substances. However, none the granulating techniques heretofore proposed have satisfactory effects (e.g., granule strength, particle size, and solubility).

That is, as the granulating techniques for the granular agents, melt granulation methods, extrusion granulation methods, compression granulation methods, tumbling granulation methods, spary cooling methods, fluidized bed granulation methods and the like are generally utilized. Furthermore, a large amount of binder is used for further controlling the solubility according to spray cooling method and extrusion granulating method. On the other hand according to tumbling granulation method and fluidized bed granulation method a relatively small amount of binders is used. However, these granulating methods have the following problems.

Spray Cooling Granulation Method and Extrusion Granulation Method

According to these methods, since the physiologically active substances are sprayed or extruded as slurries, the protective binders must be used in an amount of 45% by weight or more to fluidize the physiologically substances. The use of such a too large amount of binders causes a solubility problem in the abomasum or downstream thereof.

Although the addition of a solubility modifier has be made in an attempted to eliminate this problem, any improvement in the solubility is limited because the modifier powder particles are covered by the binder. Furthermore, since the physiologically active substances are uniformly included in the granular agents, the physiologically active substances near the surface are likely to be dissolved and, therefore, are disadvantageously lost.

Tumbling Granulation Method

According to this method, since good granulating agents cannot be produced unless the core materials having a certain size, granular agents have a size of less than 1 mm are difficult to produce and the amount of physiologically active substances contained in the granules is limited because of the presence of the core material. Furthermore, since the physiologically active substances are present only in or near the surface, the dissolving percentage in a rumen becomes high unless the granules are subjected to a certain treatment.

As mentioned above, according to this method, although the amount of binder can be decreased, compared to the spraying and extrusion methods, the solubility in a rumen becomes disadvantageously large.

Fluidized Bed Granulation Method

According to this method, particles are kept under fluidization conditions and binders and powder are added, followed by granulation. However, the dense granules are difficult to produce and the strength of the granules is weak because the force acted on the granules during the granulation is weak, compared to the tumbling or agitating granulation methods. Furthermore, since the porosity of the granules is high and thus it is very probable that the granules will be impregnated with a rumen liquor, the granules are likely to disintegrate and dissolve when retained in a rumen for a long time.

Compression Granulating Method

According to this method, although granules can be produced either with a large amount of binders or with a small amount of binders, the sizes of producable granules are limited. For example, the production of granules having a particle size of less than 2 mm is difficult. When the size of the granules is large, it is very probable that the granules will be ruminated and crunched, and thus the dissolving loss in a rumen is disadvantageously increased. When the amount of binder is large, disadvantages arise similar to those of the above-mentioned spray cooling granulation method. On the other hand, when the amount of binder is small, the porosity of the resultant granules becomes high and, therefore, the solubility in a rumen becomes disadvantageously high.

To solve the above-mentioned problems or disadvantages of conventional granulating methods, granular agents obtained by coating the surface of particles of physiologically active substances and binders with a material insoluble in a rumen have been proposed (see JP-B- No. 60-258112). However, according to this method, since a large amount (e.g., 5 to 45% by weight) of a coating agent is used for coating the physiologically active substances, the binders and the coating agent are present at the surface and, therefore, the effective components are dissolved and lost in a rumen, as in the above-mentioned methods. Furthermore, the amount of effective components in the granules is disadvantageously decreased with the addition of the coating agents.

SUMMARY OF THE INVENTION

Accordingly, the objects of the present invention are to eliminate the above-mentioned disadvantages of the prior art and to provide a granular agent for a ruminant and, containing a physiologically active substance, which:

(1) will not easily dissolve in a rumen, but can be almost entirely dissolved in an abomasum and downstream thereof;

(2) has as large an effective component content as possible and a substantially high availability of the effective component; and (3) has an optimum size, density, and such that there are a low probability of the granules being crunched during the rumination and such that the granules smoothly reach an abomasum and downstream thereof without disintegration.

Another object of the present invention is to provide a method for producing the above-mentioned granular agent for a ruminant, in which:

(1) a protective substance, i.e., as small as possible amount of a binder in the inside of the granules is used (2) a dense binder layer is formed in the surface of the granules to form a double layer structure so that the physiologically active substance is not present in the surface; and (3) defective points are intentionally formed in the dense surface layer to increase the availability of the physiologically active substances.

Other objects and advantages of the present invention will be apparent from the following description.

In accordance with the present invention, there is provided a granular agent for a ruminant comprising a solid substance containing at least one physiologically active substance coated with a thin film of a waxy substance having a melting point of 40° C. to 120° C., the thin film having a thickness of 0.2 to 20 μm and containing therein fine solid particles having a melting point of 120° C. or more and an average particle size of 10 μm or less, and the fine solid particles being substantially slightly soluble in water and insoluble in the waxy substance under a neutral condition.

In accordance with the present invention, there is also provided a method for producing a granular agent for a ruminant according to claim 1 comprising granulating, with stirring, at least one solid physiologically active substance in the presence or absence of a solid auxiliary by using, as a binder, 20% to 35% by weight, based on the total amount of the granular agent, of a waxy substance having a melting point of 40° C. to 120° C., and adding 0.02% to 5% by weight, based on the total amount of the granular agent, of a fine solid particle having an average particle size of 10 μm or less and a melting point of 120° C. or more, which is substantially slightly soluble in water and insoluble in the waxy substance, when a thin film of the waxy substance is being formed on the surface of the granulating solid containing the physiologically substance, whereby the fine solid particles are included in the surface thin layer portion of the granular agent.

BRIEF DESCRIPTION OF THE DRAWING

The present invention will be better understood from the description set forth below with reference to the accompanying drawings, in which:

FIG. 1(a) is a schematic crosssectional view of a granule having a surface layer formed without including fine solid particles;

FIGS. 1(b) to 1(e) are schematic crosssectional views of granules each having a surface layer formed which includes fine solid particles;

FIG. 2 graphically illustrates the distribution of the fine solid particles in the surface layers of the granules; and FIG. 3 is a schematic crosssectional view of the granule, for explaining the positions (A), (B), and (C) in the abscissa axis of FIG. 2.

DESCRIPTION OF THE PREFERRED EMBODIMENT

In the granular agents produced by spray granulation and extrusion granulation, since the inside physiologically active substances and various additives are uniformly distributed, the solubilities at the inside and the outside of the granules are substantially identical. Accordingly, when the granules are not easily dissolved in a rumen, the granules are also not easily dissolved in an abomasum and downstream thereof. Thus, it is difficult to separately control the solubilities in the rumen and the abomasum.

Accordingly, the present inventors have made an intensive study of an agitating granulation method as a method for separately controlling the structures of the surface and the inside of the granules and, as a result, found that the defects in the strength of conventional granules obtained by this method due to the presence of pores (i.e., pin holes) can be solved by forming a dense layer on the surface of the granule by appropriately selecting the kinds and amounts of binders, the agitation time, and the granulating temperature, and by including the fine solid particles in the surface layer. Furthermore, according to the present invention, the resultant granular agents are quickly disintegrated in an abomasum and downstream thereof.

The present invention will now be explained in detail.

Physiologically Active Substance

The physiologically active substances to be granulated in the present invention are those useful as nutrient sources for ruminants or useful for the prevention or treatment of ruminants' diseases. Examples of such substances are as follows:

(1) Natural amino acids and the derivatives thereof:

Methionine, lysine, tryptophane, threonine, and other amino acids usable as feed additives, N-acylamino acids, hydroxy homologue compounds, and physiologically acceptable salts thereof, such as hydrochlorides, hydrosuefates, ammonium salts, pottasium salts, calcium salts, megnesium salts and sodium salts of amino acids;

(2) Vitamins and the derivatives thereof:

Vitamin A, vitamin A palmitate, vitamin A acetate, β-carotene, vitamin D ($D_2$, $D_3$, $D_4$), vitamin E, menadione sodium bisulfite, vitamin Bs (thiamin, thiamin hydrochloride, riboflavin, nicotinic acid, nicotinic amide, calcium pantothenate, pantothenate choline, pyridoxine hydrochloride, cyanocobalamin, biotin, folic acid, p-aminobenzoic acid), vitamin K, vitamin Q, vitamin F, vitamin C., etc.

(3) Enzymes:
protease, amylase, lipase, cellurase, other physiologically effective enzymes, etc.

(4) Animal drugs:
Tetracycline type, amino sugar type, and macrolide type antibiotics; other drugs such as polypeptide type and, polysaccharide type drugs; antiparasitics such as negphon; piperazine salts; etc.

(5) Hormones:
Estrogen, stilbestrol, hexestrol, tyroprotein, goitradien, etc.

(6) Nutrient sources:
Proteins, carbohydrates, etc.

(7) Effective microorganisms:
Lactobacillus, Lactobacillus bifidus, and yeasts such as brewers' yeast.

(8) Various minerals:

These physiologically active substances may be used alone or in any combination thereof, but the use of a substance having a large hygroscopicity is not preferable. Although there are no specific limitations to the amount of the physiologically active substances, the preferable amount is 15% to 60% by weight, more preferably 20% to 40% by weight, based on the total weight of the granular agent.

Binder

The binders usable in the present invention are waxy substances having a melting point (or a solubility point) of 40° C. to 120° C., preferably 60° C. to 90° C. According to the present invention, those binders which will not cause problems when fed as an animal feed additive to animals, and which do not adversely affect, or are not reactive with the physiologically active substances in the granular agent, are used, as follows:

(1) Waxes of hydrogenated vegetable fats and animal fats which are not soluble in water under neutral conditions:
Tallow, Rice wax, Japan wax, beeswax, candelita wax, carnauba wax, lanolin, etc.

(2) Saturated and unsaturated monocarboxylic acids having 14 to 22 carbon atoms:

(3) Sucrose esters, glycerol fatty acid esters (di, tri, mono), propylene glycol fatty acid esters, sorbitan fatty acid esters, etc.

Although there are no critical limitations to the amount of waxy substance to be used in the present granular agent, the preferable amount is 10% to 35% by weight, more preferably 15% to 30% by weight, based on the total amount of the granular agent. When the amount of the waxy substance is less than 10% by weight, the granulation is likely to be difficult or the formation of a film having a thickness of 0.2 μm or more is likely to be difficult even when granulated. On the other hand, when the amount of the waxy substance is more than by weight, not only is the thickness of the film likely to be increased but also the solubility in an abomasum and downstream thereof tends to be decreased due to the increase in the amount of the internal binder.

Furthermore, when the melting point (or solubilizing point) of the waxy substance to be used is less than 40° C., since the resultant granular agent is melted or softened in a rumen, the desired rumen-by-pass effects cannot be obtained. Contrary to this, when the melting point (or solubilizing point) is more than 120° C., many physiologically active substances become unstable and are deactivated or denatured due to a high temperature during the granulation. Consequently, the granulation under a temperature of 120° C. or less is practical.

Solubility Modifier and Other Auxiliary Substance

According to the present invention, auxiliaries, which are stable under neutral conditions (i.e., pH=6-8) in a rumen during the granulation, but are disintegrated grated or solubilized under acidic conditions (i.e., pH=3 or less) in an abomasum and downstream thereof, are optionally used during the granulation. Furthermore, auxiliaries capable of appropriately controlling a density of the final granular products to a desired range can be usefully utilized.

The density of the granular agent according to the present invention is preferably adjusted to 1.0 g/cm$^3$ or more, more preferably 1.2 to 2.0 g/cm$^3$ especially 1.2 to 1.6 g/cm$^3$. When the density is less than 1.0 g/cm$^3$, the retention time of the granular agent in a rumen becomes long and the amount of granular agent dissolved in a rumen becomes large.

Examples of auxiliary substances usable in the present invention are at least one substance selected from the following substances:

(1) Carbonates:
Calcium carbonate, magnesium carbonate, cobalt carbonate, aluminum carbonate, etc.;

(2) Inorganic phosphorus salts:
Tribasic calcium phosphate, dibasic calcium phosphate tribasic magnesium phosphate, dibasic magnesium phosphate, zinc phosphate, aluminum phosphate, calcium silicate, calcium pyrophosphate, etc.;

(3) Metallic Oxides:
Magnesium oxide, calcium oxide, etc.;

(4) Polysaccharides:
Chitosan, chitin, calcium alginate, carageenan, etc.;

(5) Synthetic Polymer Substances:
Cellulose derivatives such as benzylaminomethyl cellulose, dimethylaminomethyl cellulose, piperidylhydroxyethyl cellulose, cellulose acetate diethylamino acetate, cellulose acetate dibutylamino hydroxypropyl ether, etc.; polyvinyl derivatives such as vinyl-diethylamine-vinyl acetate copolymer, vinylbenzylaminevinylacetate copolymer, poly(vinyldiethylamino acetacetal), vinylpiperidyl acetacetal-vinyl acetate copolymer, poly(vinyl acetaldiethylamino acetate), poly(dimethylamino ethyl methacrylate), poly(diethylamino methylstyrene), poly(vinyl ethylpyridine), vinyl ethylpyridine styrene copolymer, vinyl ethylpyridine acrylonitrile copolymer, methyl vinylpyridine styrene copolymer, etc.

Of the above-mentioned auxiliary substances, magnesium oxide, calcium carbonate, and calcium oxide, especially magnesium oxide, are preferably used. Although there are no critical limitatives to the amount of auxiliary substance, the auxiliary substance is preferably used in an amount of 30% to 50% by weight, more preferably 35% to 45% by weight, based on the total amount of the granular agent. When the amount of the auxiliary substance is less than 30% by weight, the durability in a rumen is likely to worsen. Contrary to this, when the amount is more than 50% by weight, the content of the physiologically active substance is likely to be decreased.

Fine, Solid Particle

Fine solid particles can be used in the present invention for forming appropriate dissolving pores during the formation of the dense surface layer of the granular agents by an agitation granulating method. These pores afford properties such that the granules are not disintegrated in a rumen, but the granules are disintegrated in an abomasum and downstream thereof due to the presence of the pores.

When the granular agent is produced with a wax type binder by an agitation granulating method, a binder surface layer can be fored in the surface of the granules depending upon the conditions such as the optimum binder amount, agitation time, agitation load, and temperature. When fine particles are further added thereto, followed by agitating, the fine particles are included in the binder layer and enter into the inside with the elapse of time, whereby the surface layer is appropriately roughened, and the pores are formed therein.

The typical various distributions of the fine particles in the surface layer are schematically shown in FIGS. 1(b) to 1(e) and FIG. 2. The solubility can be controlled by obtaining a constant distribution of the fine particles.

When the fine particles are not added, the resultant granular agents exhibit the condition shown in FIG. 1(a) when the granulation is completed. The resultant granules exhibit poor solubility under the conditions both in a rumen and in an abomasum.

On the other hand, when 1% by weight of, for example, $SiO_2$ having a particle size of 1 μm or less is added, the distribution of FIG. 1(b) is absorbed immediately after the addition and $SiO_2$ is gradually moved, with the elapse of time, as shown in the distributions of FIGS. 1(c), 1(d), and 1(e) and, finally, $SiO_2$ is concentrated into the center of the granules as shown in FIG. 1(e).

When the present inventors studied the correlation between the distributions of the fine particles and the solubilities, it has been found that the distributions shown in FIGS. 1(c) and (d) exhibit good results. That is, as shown in the curves (c) and (d) of FIG. 2, the desired good solubility of the granular agents can be obtained when the fine solid particles are present at least in a zone between the inside of the surface layer (i.e., a point C in FIG. 3) and the outer surface (i.e., a point A in FIG. 3).

The fine solid particles to be included in the surface layer are those which are substantially only slightly soluble in water under neutral conditions and insoluble in the waxy substance of the binder and which are not melted at a granulation temperature (i.e., a melting point of 120° C. or more).

Examples of such fine particles usable in the present invention are those having an average particle size of at least 10 μm or less, preferably 1 μm or less (i.e., a sub-micron particle) selected from, for example, the following substances:

(1) Oxides:
Silicon oxide, aluminum oxide, magnesium oxide, titanium oxide, etc.;

(2) Carbonates:
Calcium carbonate, magnesium carbonate, aluminum carbonate, cobalt carbonate, etc.;

(3) Inorganic phosphorus salt:
Tribasic calcium phosphonate, dibasic calcium phosphate, tribasic magnesium phosphate, dibasic magnesium phosphate, calcium pyrophosphate, calcium silicate, etc.;

(4) Metal Salts of Fatty Acid:
Calcium stearate, magnesium stearate, zinc stearate, calcium lactate, magnesium citrate, etc.;

These substances may be used alone or in any mixture thereof.

The preferable amount of the fine solid particles added is found to be 0.02% to 5% by weight in view of the fact that the film strength should be retained without weakening the strength. When the amount is less than 0.02%, the solubility in an abomasum is likely to be insufficient. Contrary to this, when the amount is more than 5%, the solubility of the granular agent in a rumen is likely to be increased and the strength of the granular agent tends to be decreased.

The particle size of the fine solid particles are preferably selected based on the thickness of the film formed on the surface of the granules. For instance, when the particles having a particle size of preferably at least one half (½) or less, more preferably one tenth (1/10) or less of the thickness of a film formed on the surface of the granule are used, the desired uniform surface layer can be advantageously formed.

When the average particle size of the fine solid particles used is more than 10 μm, the desired durability in a rumen cannot be obtained irrespective of the substances, probably because the defects of the surface layer becomes large.

Granulation Method

According to the present invention, the desired granular agent can be granulated using any conventional granulators capable of controllably heating the waxy substance used as a binder to a given temperature more than the melting point. The heating can be either electric heating or warm water or steam heating. Preferably, an agitation granulator having a structure capable of heating as uniformly as possible is used.

As a granulating method, conventional agitation granulating methods can be directly used, except that the above-mentioned fine solid particles are added at the time when the dense layer of the waxy substance is being formed on the surface. The granulation should be completed when a thin film having the predetermined thickness is formed.

Namely, for example, a granulator maintained at a temperature of a melting point of a binder or more, preferably a temperature of a melting point +5° C. or more is used. Then, one or more of the above-mentioned solid physiologically active substances, with or without the auxiliary substance, are added, while the waxy binder substances are added in the form of a powder or in the molten state previously prepared, preferably by a spraying method, whereby an agitation granulating is effected. Thus, the solid physiologically active substances and the other additives are granulated and, while a thin film of the waxy substance is being formed, the fine solid particles are added.

As a result of variously studying the correlation between the thickness of the thin film, the appropriate film thickness is found to be 0.2 to 20 μm. When the thickness is less than 0.2 μm, the solubility of the granular agent becomes remarkably unstable, and the desired good granular agent may not be obtained. Contrary to this, when the thickness is more than 20 μm, the solubility in an abomasum is remarkably decreased.

Although the agitation and granulation time may largely vary depending upon the physical properties of the addition substances to be used, the preferable condition can be selected so that the film thickness becomes 0.2 to 20 μm and the granulation yield becomes optimum. The typical agitation and granulation time is 20 to 60 minutes.

Furthermore, after granulation and after once cooling, as a final step, the surface of the granular agent may be optionally coated with another wax having a melting point of less than a temperature of the melting point (T) of the granulating wax minus 10° C. (i.e., T° C. −10° C.) to provide a protective layer.

Furthermore, the granular agent may be optionally further coated with a substance insoluble in neutral water but soluble in acidic water, to provide a protective layer.

The preferable particle size of the final granular agent of the present invention is as small as possible so that the probability of crunching and the probability of ruminating are decreased when fed or ruminated by a ruminant. Accordingly, the size is preferably 3 mm or less, more preferably 0.5 mm to 3 mm, especially 0.5 mm to 2 mm. When the size becomes less than 0.5 mm, the durability in a rumen tends to be lowered.

As explained above, according to the present invention, the granular agent for a ruminant having a low solubility in a rumen and capable of rapidly disintegrating in an abomasum and downstream thereof and the production method thereof can be provided by embedding the specified fine solid particles in a dense surface layer formed when the granulation is carried out by selecting the amount and kind of the binder and the agitating temperature and time.

For example, the following effects can be obtained according to the present invention.

(1) The granular agent having a low solubility under neutral conditions (i.e., pH=6-8) in a rumen, when compared with conventional methods, but capable of easily dissolving under a pH of 3 or less in an abomasum and downstream thereof, can be readily obtained.

(2) Since an agitation granulating method, in which a physiologically active substance is brought into contact with a wax only for a short period of time, is used, the physiologically active substance is not denatured and is stable, when compared to a spray cooling method.

(3) The addition rates (or percentages) of, for example, a density modifier, a solubility modifier, a bulking filler, and other auxiliary additives can be increased because the necessary amount of binder can be decreased when compared to a spray method and, therefore, the freedom of granulation can be increased.

(4) Since the desired film of a binder layer can be formed in the surface of the granular agent by an agitation granulating method, the system is very simple, without necessitating the combined use of other methods.

EXAMPLES

The present invention will now be further illustrated by, but is by no means limited to, the following Examples.

EXAMPLES 1 TO 9 AND COMPARATIVE EXAMPLES 1 TO 5

Granular agents having an average particle size of 840 μm were prepared from tryptophane, lysine, or methionine, as a physiologically active substance, hydrogenated tallow oil, rice wax, beeswax, or stearic acid, as a binder, a bulking agent, a solubility modifier, or other substances listed in Table 1 (The amounts shown in Table 1 are all % by weight, based on the total weight of the granular agents) by an agitation granulating method, followed by including or embedding fine $SiO_2$ particles in the binder surface layer by the addition of the $SiO_2$ particles while the surface layer is being formed.

The granulator used was a granulator LMA-10 available from Nara Kikai K. K. (Japan) modified so that the granulator could be heated with steam or hot water and the granulation was carried out under the conditions of a temperature of the melting point of the binder plus 10° C. or more, a revolution number of a main axis of 200 rpm, and a revolution number of a chopper of 3000 rpm.

The film thickness of the surface layer, the distribution of $SiO_2$ in the surface layer, and solubilities under rumen and abomasum conditions were determined.

The results are shown in Table 1.

The solubilities were determined by the following in vitro method.

In vitro method

A 1.00 g amount of the granular agent was accurately weighed and was placed in a 200 ml conical flask, and 50 ml of solubilizing liquid (i.e., rumen condition liquid or abomasum liquid condition liquid, each having the composition shown below) was then added thereto. The mixture was shaken at a temperature of 39° C. for 18 hours in a high temperature shaking machine, and thereafter, the liquid and the remaining solid were recovered and the dissolved percentage was determined.

Rumen Condition Solution: NaCl (2.6 g), KCl (0.2 g), $CaCl_2 \cdot 2H_2O$ (0.01 g), $MgSO_4 \cdot 7H_2O$ (0.1 g), $Na_2HPO_4 \cdot 12H_2O$ (15 g), and $KH_2PO_4$ (2 g) were dissolved in 1000 cc of pure water to prepare a solution having a pH of 7.4.

Abomasum Condition Solution: Gly (7.5 g) and NaCl (5.84 g) were dissolved in 1000 cc of pure water, followed by adjusting a pH of the solution to 2 with 0.1N HCl.

TABLE 1

| No. | Physiologically Active Substance | Binder | Other Substance | Average Film Thickness (μm) | Amount of $SiO_2$ Added (%) | Type of Distribution | Solubility Rate (%) Rumen Condition | Solubility Rate (%) Abomasum Condition |
|---|---|---|---|---|---|---|---|---|
| Example 1 | Tryptophane 30% | Hydrogenated tallow oil 30% | MgO 40% | 5 | 0.02 | (c) | 5.9 | 86.1 |
| Example 2 | Tryptophane 30% | Hydrogenated tallow oil 30% | MgO 40% | 5 | 0.5 | (d) | 10.1 | 84.3 |
| Example 3 | Tryptophane 30% | Hydrogenated tallow oil 30% | MgO 40% | 5 | 1.0 | (d) | 13.3 | 87.0 |
| Example 4 | Tryptophane 40% | Hydrogenated tallow oil 25% | MgO 35% | 3 | 0.5 | (d) | 12.9 | 89.2 |
| Example 5 | Tryptophane 30% | Hydrogenated tallow oil 30% | MgO 40% | 10 | 0.5 | (c) | 8.7 | 79.4 |
| Example 6 | Tryptophane 30% | Rice wax 28% | $CaCO_3$ 42% | 4 | 0.5 | (d) | 14.5 | 87.9 |

TABLE 1-continued

| No. | Physiologically Active Substance | Binder | Other Substance | Average Film Thickness (μm) | Amount of SiO$_2$ Added (%) | Type of Distribution | Solubility Rate (%) Rumen Condition | Solubility Rate (%) Abomasum Condition |
|---|---|---|---|---|---|---|---|---|
| Example 7 | Tryptophane 30% | Stearic acid 30% | MgO 40% | 6 | 0.5 | (d) | 9.4 | 79.6 |
| Example 8 | Methionine 30% | Hydrogenated tallow oil 30% | MgO 40% | 5 | 0.5 | (d) | 11.0 | 82.2 |
| Example 9 | Methionine 30% | Beeswax 30% | MgO 40% | 5 | 0.5 | (d) | 10.7 | 84.5 |
| Comparative Example 1 | Tryptophane 30% | Hydrogenated tallow oil 30% | MgO 40% | 5 | 0.005 | (c) | 4.2 | 53.9 |
| Comparative Example 2 | Tryptophane 30% | Hydrogenated tallow oil 30% | CaCO$_3$ 40% | 5 | 2.0 | (c) | 32.1 | 91.6 |
| Comparative Example 3 | Tryptophane 30% | Hydrogenated tallow oil 30% | MgO 40% | 5 | 0 | (a) | 5.3 | 47.0 |
| Comparative Example 4 | Tryptophane 30% | Hydrogenated tallow oil 30% | MgO 40% | 5 | 0.5 | (e) | 7.3 | 61.5 |
| Comparative Example 5 | Tryptophane 30% | Hydrogenated tallow oil 30% | MgO 40% | 5 | 0.5 | (b) | 9.4 | 65.7 |

As is clear from the results shown in Table 1, the granular agents of Examples 1 to 9 according to the present invention exhibited a low solubility under the rumen condition, but a high solubility under the abomasum condition. Contrary to this, when the amount of SiO$_2$ was low as in Comparative Example 1, when no SiO$_2$ was used as in Comparative Example 3, when the granular agent was recovered immediately after the addition of SiO$_2$ as in Comparative Example 4, and when the agitation was operated for too much time to granulate fine particles so that SiO$_2$ was completely trapped in the inside of the granules as in Comparative Example 5, the solubilities in the rumen and/or abomasum conditions was unpreferably poor.

On the other hand, when a large amount of SiO$_2$ was used as in Comparative Example 2, the practical effectivity was decreased because the solubility in a rumen was remarkably high.

We claim:

1. A solid granular agent for a ruminant consisting essentially of:
   (i) 15% to 60% by weight of at least one physiologically active substance,
   (ii) 10% to 35% by weight of a waxy substance having a melting point of 40° C. to 120° C.,
   (iii) 30% to 50% by weight of a solid auxiliary substance, which is stable under a neutral condition and is disintegrated or dissolved under an acidic condition, and
   (iv) 0.02% to 1.0% by weight, of fine solid particles having an average particle size of 10 μm or less and a melting point of 120° C. or more, which is substantially slightly soluble in water and insoluble in the waxy substance, said granular agent being prepared by granulating components (i), (ii), and (iii) in a one-step agitation granulating method, followed by adding component (iv), whereby the physiologically active substance (i) is coated with a thin film of the waxy substance (ii) having a thickness of 0.2 to 20 μm and containing the solid auxiliary substance (iii) therein and the fine solid particles (iv) are embedded in the surface thin film of the granular agent.

2. A granular agent as claimed in claim 1, wherein the density of the granular agent is 1.0 g/cm$^3$ or more.

3. A granular agent as claimed in claim 1, wherein the particle size of the granular agent is 0.5 mm to 3 mm.

4. A granular agent as claimed in claim 1, wherein the auxilary substance solid substance is magnesium oxide and/or tribasic calcium phosphonate and/or dibasic calcium phosphonate.

5. A granular agent as claimed in claim 1, wherein the fine solid particles (iv) are silicon dioxide powder particles.

* * * * *